US00PP17239P2

(12) United States Plant Patent
Doguet et al.

(10) Patent No.: US PP17,239 P2
(45) Date of Patent: Nov. 28, 2006

(54) BUFFALOGRASS PLANT NAME 'MB'

(50) Latin Name: *Buchloe dactyloides (Nutt) Engelm*
Varietal Denomination: MB

(76) Inventors: David Doguet, 1602 Continental, Pleasanton, TX (US) 78064; Virginia Gail Lehman, 811 Mountain River Dr., Lebanon, OR (US) 97355

( * ) Notice: Subject to any disclaimer, the term of this patent is extended or adjusted under 35 U.S.C. 154(b) by 9 days.

(21) Appl. No.: 11/327,456

(22) Filed: Jan. 9, 2006

(51) Int. Cl.
*A01H 5/00* (2006.01)

(52) U.S. Cl. ..... Plt./391

(58) Field of Classification Search ..... Plt./391
See application file for complete search history.

(56) References Cited

U.S. PATENT DOCUMENTS

| | | | |
|---|---|---|---|
| PP7,539 | P | 5/1991 | Engelke et al. |
| PP8,475 | P | 11/1993 | Riordan et al. |
| PP11,004 | P | 7/1999 | Doguet |
| PP11,373 | P | 5/2000 | Riordan et al. |
| PP12,910 | P2 | 9/2002 | Wu et al. |

*Primary Examiner*—Anne Marie Grunberg
*Assistant Examiner*—Annette H Para

(57) ABSTRACT

An asexually reproduced variety of male or staminate perennial buffalograss distinguished by a unique combination of characters including fine leaf blade width and high tiller number at stolon nodes.

2 Drawing Sheets

Latin name of the genus and species of the plant claimed: The present invention relates to the genus and species *Buchloe dactyloides* (Nutt) *Engelm.*
Variety denomination: 'MB'.

BACKGROUND OF THE INVENTION

Field of Invention

The present invention relates to a new and distinct asexually reproduced variety of perennial *Buchloe dactyloides* (*Nutt*) *Engelm*.

BRIEF SUMMARY OF THE INVENTION

BACKGROUND OF THE INVENTION

This invention relates to a new and distinct perennial male or staminate buffalograss cultivar identified as 'MB' (herein referred to as 'MB'). The inventors, David Doguet and Virginia G. Lehman, discovered 'MB' under cultivated conditions in a mowed roadside area near Houston, Tex. 'MB' was identified as a distinctly different vegetative male patch or segregated clonal plant differing by much higher tiller density than the surrounding male clones, or any other male clones known in the inventors knowledge. The inventors asexually reproduced 'MB' by taking vegetative cuttings of the plant material including stolons and tillers, cutting the stolons into segments, each with a vegetative bud, and rooting them in field nurseries at Bladerunner Farms, Inc. nurseries near Poteet, Tex. Stolons and vegetative plugs of 'MB' were asexually reproduced and moved to the greenhouse and field nurseries near Lebanon, Oreg. for further evaluation.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Buffalograss plant named 'MB'.

BRIEF DESCRIPTIONS OF THE ILLUSTRATIONS

Figure 1:
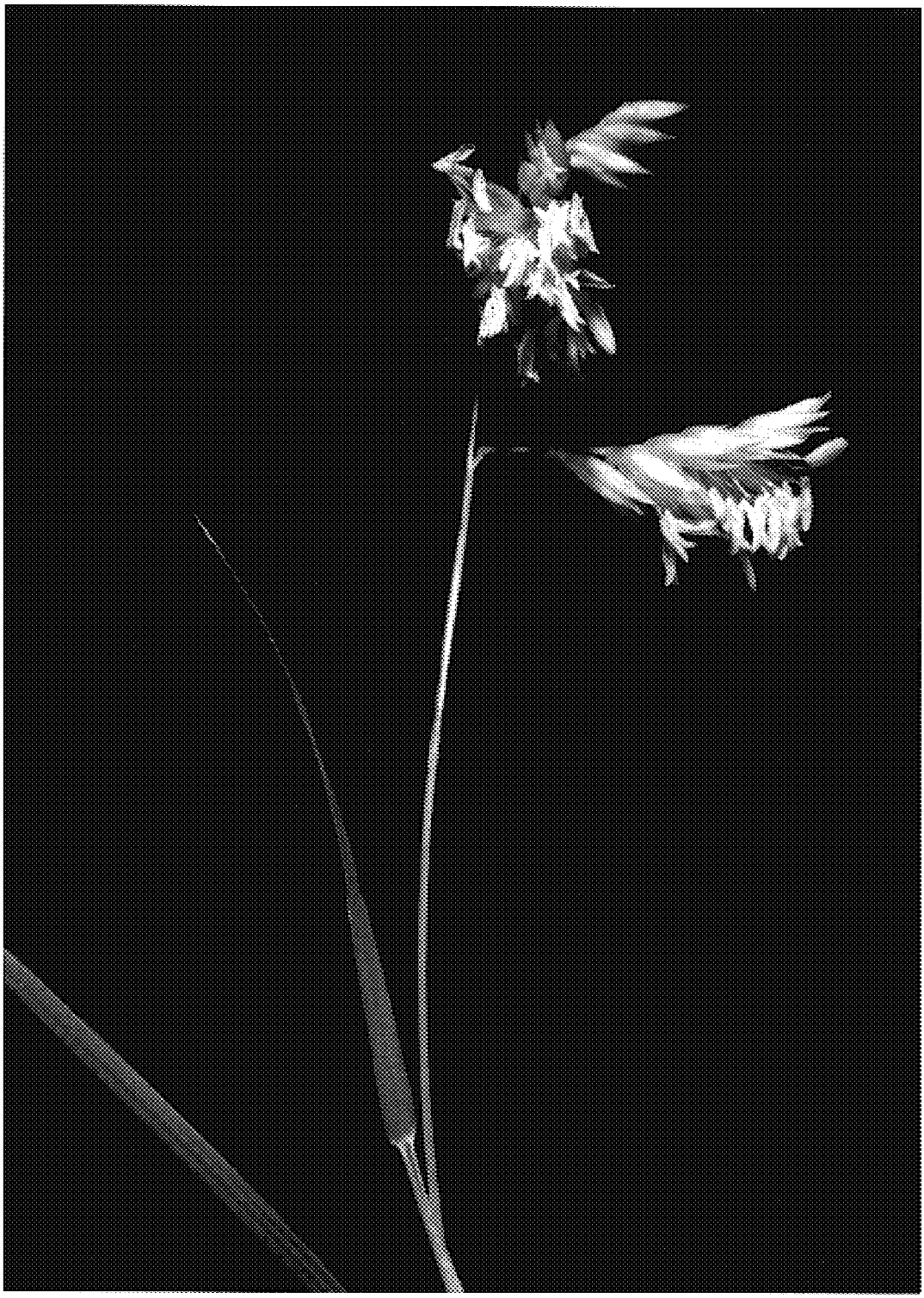

FIG. 1. Inflorescence of 'MB' buffalograss.

Figure 2:
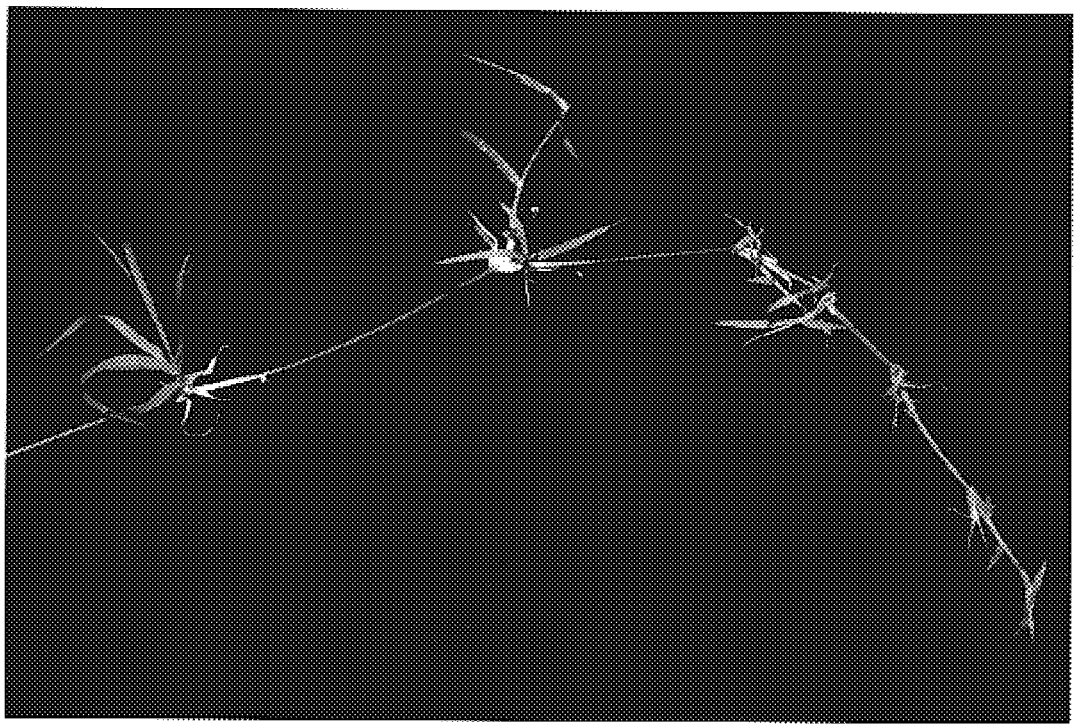

FIG. 2. Stolon of 'MB' buffalograss.

COMPLETE DESCRIPTION OF THE VARIETY

'MB' was characterized in greenhouse and field conditions. 'MB' is a unique male or staminate variety of buffalograss (*Buchloe dactyloides* (Nutt) Engelm.) that was discovered under cultivated conditions in a mowed roadside area near Houston, Tex. 'MB' was identified as having a much higher tiller density than the surrounding male buffalograss clones, or any other male clones known in the inventor's knowledge. The mowed roadside was located in USDA Plant Hardiness Zone 9a. 'MB' was propagated by the inventors under field and greenhouse conditions in Poteet, Tex. and Lebanon, Oreg. by cutting of stolons, rooting them in soil, and planting of the rooted material to provide planting stock for studying performance and for comparison of morphological characters after propagation. 'MB' has been propagated by stolons, tillers, and sod. Asexually reproduced plants of 'MB' have remained stable and true to type through successive generations of propagation. No female inflorescence has been noted from 'MB', and as a consequence, no seed has been produced from 'MB'.

'MB' is a perennial buffalograss that spreads by stolons and tillers. Characteristics of 'MB' measured in 2005 were taken from plants that were approximately 15 months in age. The greenhouse was located near Lebanon, Oreg., with a nighttime low temperature of 50 degrees F., and daytime high of 80 degrees F., and a minimum soil temperature of 77 degrees F. The plants were grown with a minimum 14-hour day length, supplemented with photosynthetically active radiation equivalent to approximately 50% sunlight. The plants were fertilized with the equivalent of 1 pound of actual N per month, using a soluble fertilizer of 20-20-20 in two equal soluble applications per month.

'MB' has a shorter canopy height than '609' U.S. Plant Pat. No. 8,475 (Table 1) when measured under greenhouse conditions in Lebanon, Oreg., 2005. Most significantly, 'MB' has more tillers per stolon node than either Prairie or '609', a positive trait when the turfgrass is harvested for sod production. 'MB' has shorter internode lengths (Table 2), providing a higher density turfgrass. As a male or staminate clone, no burrs with seeds of 'MB' have developed; no seedlings have been noted in field production area or field test areas. The inflorescences produced in the greenhouse have consisted of a staminate structure or male with anthers. The anthers have been observed to shed pollen; it is possible that 'MB' would fertilize a receptive female buffalograss but this has not been observed, nor tested. 'MB' has retained the unique characters during successive stages of propagation and has shown to be a stable variety in asexual propagation.

'MB' has shown susceptibility to buffalograss mite, [*Eriophyes slykhuisi* (Hall)] in test plots near Poteet, Tex. 'MB' has not shown susceptibility to any diseases or other insects such as mealybug. 'MB' shows turf density higher than 'Prairie' or '609', and when harvested as sod, maintains sod block integrity. 'MB' is adapted North/South from the Kansas-Oklahoma border through Mexico, and East/West from Missouri to California. 'MB' is similar to most buffalograsses in water use demands, having excellent long term drought survival. 'MB' is adapted from sandy to heavier loam soil textures and from slightly acid to slightly alkaline soil pH.

TABLE 1

Leaf blade widths and lengths and texture class of selected buffalograss cultivars, measured under greenhouse conditions in Lebanon, OR, 2005.

| Variety | Clonal Sex | Canopy Height cm | Tillers per stolon node Number | Width, 4th youngest non-flowering stolon leaf mm | Leaf Sheath Length, non-flowering stolon cm |
|---|---|---|---|---|---|
| 'MB' | Male | 8.2 | 3.7 | 1.5 | 0.6 |
| '609' | Female | 17.8 | 1.5 | 1.4 | 1.0 |
| 'Prairie' | Female | 7.0 | 1.8 | 1.1 | 0.8 |

TABLE 2

Inflorescence and leaf characters of selected buffalograss cultivars, measured under greenhouse conditions in Lebanon, OR, 2005.

| Variety | Internode Length, 1st to 2nd stolon node cm | Internode Length, 2nd to 3rd stolon node cm | Anther length mm | Hair length, mouth of leaf sheath mm |
|---|---|---|---|---|
| 'MB' | 1.9 | 1.8 | 1.7 | 1.9 |
| '609' | 4.1 | 5.4 | Absent | 3.0 |
| 'Prairie' | 3.8 | 6.1 | Absent | 2.7 |

COMPLETE BOTANICAL DESCRIPTION OF THE VARIETY

Origin: 'MB' is a cultivar of a single male clone discovered under cultivated conditions near Houston, Tex. in a mowed roadside area with many native buffalograss clones present in the area.

Classification: *Buchloe dactyloides* (Nutt) Engelm.

Growth habit: 'MB' is a perennial male clone that spreads by stolons and tillers and produces a fine textured turfgrass with a highly fibrous root system. The inflorescence of 'MB' is a staminate inflorescence with yellow to yellow-orange anthers 1.7 mm in length.

Leaf blade: Rolled in the bud, mostly flat with some with a slightly concave surface.

Leaf blade pubescence: Few hairs on adaxial surface, none on abaxial surface.

Leaf sheath pubescence: Absent with few hairs on mouth of sheath, mean length: 1.9 mm; (Prairie: 3.0; '609': 3.0).

Leaf blade margin: Rough.

Leaf blade veins: Obscure.

Vegetative leaf, fourth youngest vegetative leaf:

*Blade length range.*—0.7 cm to 3.2 cm, mean length: 1.3 cm.

*Blade width mean.*—1.5 mm.

*Sheath length mean.*—0.6 cm.

Inflorescence characters, staminate:

*Culm total length, including floral area to node below flag leaf.*—8.1 cm.

*Culm width, stem thickness, base of floral area.*—0.3 mm.

*Anther length.*—1.7 mm.

*Node thickness, node below flag leaf.*—0.6 mm.

*Flag leaf length.*—2.0 cm.

*Flag leaf width.*—1.0 mm.

Mature plant height, including inflorescence: MB: 8.2 cm; '609': 17.8 cm.

Color notations, vegetative characters, based on The R.H.S. Colour Chart (light quality, photoperiod, and general growth of the plants affect color notations):

*Leaf blade color adaxial leaf surface.*—146A yellow green.

*Stolon color.*—59A red purple and 144B yellow green.

Color notations, floral characters, based on The R.H.S. Colour Chart (light quality, photoperiod, and general growth of the plants affect color notations):

*Anthers.*—25B orange/10A yellow.

Turf quality (rated 1–9, 9 best): 7 'MB'; '609': 6; 'Prairie': 5.

Turf color (rated 1–9, 9 best): 7 'MB'; '609': 7MB'; 'Prairie': 5.

Turf density establishment rating (rated 1–9, 9 best): 7 'MB'; '609': 6; 'Prairie': 5.

Tiller production at stolon node rating: (rated 1–9, 9 best): 7 'MB'; '609': 6; 'Prairie': 5.

What is claimed is:

1. A new and distinct variety of male or staminate buffalograss plant, substantially as described and illustrated herein, characterized particularly by a male or staminate inflorescence and high tiller production at stolon nodes.

* * * * *